US008058407B2

(12) United States Patent  
Sun et al.

(10) Patent No.: US 8,058,407 B2
(45) Date of Patent: Nov. 15, 2011

(54) PURIFICATION OF ACIDIC PROTEINS USING CERAMIC HYDROXYAPATITE CHROMATOGRAPHY

(75) Inventors: Shujun Sun, Brentwood, NJ (US); Yin Luo, Cambridge, MA (US); Priscilla Jennings, Wilmington, MA (US)

(73) Assignee: Wyeth LLC, Madison, NJ (US)

( * ) Notice: Subject to any disclaimer, the term of this patent is extended or adjusted under 35 U.S.C. 154(b) by 0 days.

(21) Appl. No.: 12/608,093

(22) Filed: Oct. 29, 2009

(65) Prior Publication Data

US 2010/0113751 A1   May 6, 2010

Related U.S. Application Data

(60) Provisional application No. 61/110,468, filed on Oct. 31, 2008.

(51) Int. Cl.
  *A61K 39/395* (2006.01)
  *C07K 16/00* (2006.01)
  *C07K 1/20* (2006.01)
(52) U.S. Cl. .................. 530/390.5; 424/177.1; 530/415
(58) Field of Classification Search ........................ None
  See application file for complete search history.

(56) References Cited

U.S. PATENT DOCUMENTS

| | | | |
|---|---|---|---|
| 5,225,538 A | 7/1993 | Capon et al. | |
| 5,399,677 A | 3/1995 | Wolfman et al. | |
| 5,428,130 A | 6/1995 | Capon et al. | |
| 5,455,165 A | 10/1995 | Capon et al. | |
| 5,514,582 A | 5/1996 | Capon et al. | |
| 5,516,964 A | 5/1996 | Umansky et al. | |
| 5,633,162 A | 5/1997 | Keen et al. | |
| 5,714,147 A | 2/1998 | Capon et al. | |
| 5,874,247 A * | 2/1999 | Toyoshima et al. | 435/69.1 |
| 6,136,310 A | 10/2000 | Hanna et al. | |
| 7,094,604 B2 * | 8/2006 | Snyder et al. | 435/457 |
| 7,122,641 B2 | 10/2006 | Vedantham et al. | |
| 2003/0165496 A1 | 9/2003 | Basi et al. | |
| 2005/0107594 A1 | 5/2005 | Sun et al. | |
| 2009/0186396 A1* | 7/2009 | Gagnon | 435/235.1 |
| 2009/0187005 A1* | 7/2009 | Gagnon | 530/344 |

FOREIGN PATENT DOCUMENTS

| | | |
|---|---|---|
| EP | 0433225 A1 | 6/1991 |
| WO | WO03/059935 A2 | 7/2003 |
| WO | WO 2004/076485 A1 | 9/2004 |
| WO | WO 2005/044856 | 5/2005 |

OTHER PUBLICATIONS

Gorbunoff, M., Protein Chromatography on Hydroxyapatite Columns, Methods in Enzymology, vol. 117, Academic, Press, Inc., 1985, pp. 370-380.*
"Macro-Prep Chromatography Supports"; Bio-Rad, 8 pages.*
Ettinger et al., "Interleukin 21 as a Target of Intervention in Autoimmune Disease", Ann Rheum Dis; 67 (Suppl III):iii83-iii86 (2008).
Franklin, S., "Removal of Aggregate From an IgG4 Product Using CHT Ceramic Hydroxyapatite", Chromatography Tech Note 2940, Bio-Rad Laboratories, Inc. (2002).
Gagnon, "Hydroxyapatite Chromatography", Purification Tools for Monoclonal Antibodies, Validated Biosystems, Chapter 5, p. 87-102 (1996).
Gorbunoff, "Protein Chromatography on Hydroxyapatite Columns", Methods Enzymol. 182:329-39 (1985).
Karlsson et al.,"Ion Exchange Chromatography", Protein Purification (VCH Publishers, Inc., New York NY) pp. 107-148 (1989).
Kennedy, "Hydrophobic-Interaction Chromatography", Current Protocols in Protein Sciences, 8.4.1-8.4.21 (1995).
Kohno, "Refolding of Recombinant Proteins", Meth. Enzymol. 185:187-95 (1990).
Lullau et al, "Develpoment of a Bioprocess for Murine Dimeric IgA Production", Biotechnology Techniques 12(6):425-430 (1998).
Ogawa et al, "Effect of pH on Gradient Elution of Different Proteins on Two Types of Ceramic Hydroxyapatite", American Laboratory 171-17K (1996).
Shepard et al.,"Discoloration of Ceramic Hydroxyapatite Used for Protein Chromatography", Journal of Chromatography A 891:93-98 (2000).
Sinacola et al,, "Rapid Refolding and Polishing of Single-chain Antibodies from *Escherichia coli* Inclusion Bodies", Protein Expression and Purification 26:301-308 (2002).
Stanker et al., "One-Step Purification of Mouse Monoclonal Antibodies from Ascites Fluid by Hydroxylapatite Chromatography", Journal of Immunological Methods 76:157-169 (1985).
Steindl, F et al. "A Simple Methods to Quantify Staphyloccal Protein A in the Presence of Human or Animal IgG in Various Samples", J. Immunol. Methods 235:61-69 (2000).
Tarditi,et al., "Selective High-Performance Liquid Chromatographic Purification of Bispecific Monoclonal Antibodies", J. Immunol. Methods 599:13-20 (1992).
Usami et al., "The Effect of pH, Hydrogen Peroxide and Temperature on the Stability of Human Monoclonal Antibody", Journal of Pharmaceutical and Biomedical Analysis 14:1133-1140 (1996).
Vola et al. "Comparision of Two Different HPLC Hydroxylapatite Matrices for Resolution of IgG Idiotypes", BioTechniques 14:650-655 (1993).
Williams et al., "Ion-Exchange Chromatography", Current Protocols in Protein Sciences, p. 8.2.1-8.2.30 (1999).
Yazaki et al., "Mammalian Expression and Hollow Fiber Bioreactor Production of Recombinant Anti-CEA Diabody and Minibody for Clinical Applications", Journal of Immunological Methods 253; 195-208 (2001).
Coppola et al. "High-Performance Liquid Chromatography of Amino Acids, Peptides and Proteins", Journal of Chromatography 476:269-290 (1989).
Giovannini et al. "Comparison of Different Types of Ceramic Hydroxyapatite for the Chromatographic Separation of Plasmid DNA and a Recombinant Anti-Rhesus D Antibody", Bio Sep 9:359-368 (2001).
Josic et al. "Purification of Monoclonal Antibodies by Hydroxylapatite HPLC and Size Exclusion HPLC", Biological Chemistry Hoppe-Seyler 372:149-156 (1991).
Stevens et al. "Techniques for Purifying Monoclonal Antibodies", American Biotechnology Laboratory 3(5):22-30 (1985).
Biorad CHT Ceramic hydroxyapatite Product Information Sheet, p. 1-4 (2002).
International Search report and Written Opinion for PCT/US2009/062528 Dec. 16, 2009.

(Continued)

*Primary Examiner* — David A Saunders

(57) ABSTRACT

The present invention provides a method of removing product-related inactive or partially active species, high molecular weight aggregates, as well as other process-related impurities from preparations of acidic proteins by using ceramic hydroxyapatite chromatography.

23 Claims, 2 Drawing Sheets

OTHER PUBLICATIONS

Giovannini et al., "Isolation of a Recombinant Antibody from Cell Culture Supernatant: Continuous Annular Versus Batch and Expanded-Bed Chromatography", Biotechnology and Bioengineering 73:522-529 (2001).

Jungbauer, A., et al "Comparison of Protein A, Protein G and Copolymerized Hydroxyapatite for the Purification of Human Monoclonal Antibodies", Journal of Chromatography 476:257-268 (1989).

* cited by examiner

SEQUENCE LISTING

<160> NUMBER OF SEQ ID NOS: 1

<210> SEQ ID NO 1
<211> LENGTH: 21
<212> TYPE: PRT
<213> ORGANISM: Apis mellifera

<400> SEQUENCE: 1

Met Lys Phe Leu Val Asn Val Ala Leu Val Phe Met Val Val Tyr Ile
1               5                   10                  15

Ser Tyr Ile Tyr Ala
            20

PURIFICATION OF ACIDIC PROTEINS USING CERAMIC HYDROXYAPATITE CHROMATOGRAPHY

CROSS-REFERENCE TO RELATED APPLICATIONS

This application claims the benefit under 35 U.S.C. §119 (e) to U.S. provisional application No. 61/110,468, filed Oct. 31, 2008, which is hereby incorporated by reference in its entirety.

FIELD OF THE INVENTION

The present invention describes a method of removing partially active and/or inactive product-derived species, high molecular weight aggregates, and other impurities from acidic proteins, e.g., Ig-fusion proteins, using ceramic hydroxyapatite chromatography. Under the specific operating binding and elution conditions provided in this invention, acidic protein product, e.g., acidic Ig-fusion protein product, can be separated from the product-derived and process-derived impurities with high resin binding capacity and good product yield.

BACKGROUND OF THE INVENTION

It is desirable to identify useful methods of purifying proteins that do not destroy, or significantly reduce, the biological activity of the protein. Contaminants must be removed from protein preparations, such as acidic protein preparations (e.g., immunoglobulin (Ig)-fusion protein preparations), before they can be used in diagnostic applications, therapeutic applications, applied cell biology, and functional studies. For instance, protein preparations, e.g., acidic protein preparations, often contain unwanted components (impurities), such as inactive and/or partially active species and high molecular weight aggregates (HMWA). Presence of inactive and/or partially active species is undesirable because these species have significantly lower binding capacity to the target compared to the active protein; thus, the presence of inactive and/or partially active species can reduce product efficacy. The formation of aggregates, e.g., HMWA, can adversely affect product safety by causing complement activation or anaphylaxis upon administration. Further, aggregate formation may hinder manufacturing processes by causing decreased product yield, peak broadening, and loss of activity.

The most common protein purification methods are predicated on differences in the size, charge, and solubility between the protein to be purified and contaminants. Protocols based on these parameters include affinity chromatography, ion exchange chromatography, size exclusion chromatography, and hydrophobic interaction chromatography. These chromatographic methods, however, sometimes present technical difficulties in the separation of aggregated or multimeric species of proteins, e.g., IgG-containing proteins. Techniques such as ion exchange and hydrophobic interaction chromatography, for instance, may induce the formation of aggregates due to an increased protein concentration or the required changes in buffer concentration and/or pH during elution. Further, in several instances proteins show differences in isoelectric points that are too small to allow for their separation by ion-exchange chromatography. Tarditi, (1992) *J. Immunol. Methods* 599:13-20. Size exclusion chromatography is cumbersome and results in the significant dilution of the product, which is a hindrance in large-scale, efficiency-based manufacturing processes. Leakage of ligands from affinity chromatography columns can also occur, which results in undesirable contamination of the eluted product. Steindl (2000) *J. Immunol. Methods* 235:61-69. Of interest, Applicants were unable to remove the inactive or partially active species using either ion exchange, e.g., anion exchange, or hydrophobic interaction chromatography.

Hydroxyapatite chromatography is a method of purifying proteins that utilizes an insoluble hydroxylated calcium phosphate $[Ca_{10}(PO_4)_6(OH)_2]$, which forms both the matrix and ligand. Functional groups consist of pairs of positively charged calcium ions (C-sites) and clusters of negatively charged phosphate groups (P-sites). The interactions between hydroxyapatite and proteins are complex and multi-mode. In one method of interaction, positively charged amino groups on proteins associate with the negatively charged P-sites, and protein carboxyl groups interact by coordination complexation to C-sites. Shepard (2000) *J. of Chromatography* 891: 93-98. Thus, acidic and basic proteins usually interact with cHA resin through different mechanisms: an acidic protein usually binds to C-sites via a coordination bond to carboxyl group, while a basic protein binds to P-sites through charge interaction with the amine group. Crystalline hydroxyapatite was the first type of hydroxyapatite used in chromatography, but it was limited by structural difficulties. Ceramic hydroxyapatite (cHA) chromatography was developed to overcome some of the difficulties associated with crystalline hydroxyapatite, such as limited flow rates. Ceramic hydroxyapatite has high durability, good protein binding capacity, and can be used at higher flow rates and pressures than crystalline hydroxyapatite. Vola et al. (1993) *BioTechniques* 14:650-655. Chromatographic separation using cHA can be performed in several distinct modes, such as binding mode, flow-through mode, or a combination binding/flow-through mode.

Hydroxyapatite chromatography has been used in the chromatographic separation of proteins, nucleic acids, as well as antibodies. However, in several instances, researchers have been unable to selectively elute antibodies from hydroxyapatite or found that hydroxyapatite chromatography did not result in a sufficiently pure product. Junbauer, (1989) *J. Chromatography* 476:257-268; Giovannini, (2000) *Biotechnology and Bioengineering* 73:522-529. A successful separation of antibodies and other basic proteins from impurities, such as HMWA, using cHA chromatography either in binding, flow-through, or combination binding/flow-through mode has been demonstrated in U.S. Publication No. 2005-0107594, incorporated herein in its entirety by reference. The present invention provides a novel method for removing product-related partially active and/or inactive species, as well as other impurities, such as HMWA, from acidic proteins, e.g., Ig-fusion proteins, using cHA chromatography techniques.

SUMMARY OF THE INVENTION

The present invention provides methods of removing impurities, such as high molecular weight aggregates, inactive and/or partially active species, as well as other impurities from acidic protein preparations using hydroxyapatite chromatography. Thus, in one embodiment of the invention, the invention provides a method for purifying at least one acidic protein of interest from a protein preparation containing impurities, wherein the method comprises applying an equilibration buffer comprising a divalent metal cation to hydroxyapatite resin, contacting the hydroxyapatite resin with the protein preparation in a load buffer, washing the hydroxyapatite resin with a wash buffer comprising the divalent metal cation, and eluting at least one acidic protein from the hydroxyapatite resin with an elution buffer comprising phosphate.

In some embodiments of the invention, the impurities are inactive and/or partially active species of the at least one acidic protein. Thus, another embodiment of the invention provides a method of purifying at least one acidic protein of interest from a protein preparation containing inactive and/or partially active species of the at least one acidic protein, comprising contacting a hydroxyapatite resin with the protein preparation; and eluting the at least one acidic protein of interest separately from the inactive and/or partially active species. Another embodiment of the invention provides a method of purifying at least one acidic protein of interest from a protein preparation containing inactive and/or partially active species of the protein of interest, comprising applying an equilibration buffer comprising a divalent metal cation to hydroxyapatite resin, contacting the hydroxyapatite resin with a protein preparation in a load buffer comprising the divalent metal cation, washing the hydroxyapatite resin with a wash buffer comprising the divalent metal cation, and eluting at least one acidic protein from the hydroxyapatite resin with an elution buffer comprising phosphate.

In at least some embodiments of the invention, the impurities are high molecular weight aggregates, and in at least one embodiment, the method of the invention results in at least about 60% reduction in high molecular weight aggregates. In other embodiments of the invention, the method results in at least about 90% reduction in high molecular weight aggregates. In additional embodiments of the invention, the impurities are protein A and/or host cell proteins. In at least some embodiments, the equilibration buffer comprises from about 1 to about 20 mM of the divalent metal cation, the load buffer comprises about 1 to about 20 mM of the divalent metal cation, the wash buffer comprises about 1 to about 20 mM of the divalent metal cation, and the elution buffer comprises about 2 to about 50 mM phosphate. In another embodiment, the elution buffer comprises about 1 to about 100 mM phosphate, or about 5 to about 50 mM phosphate or about 5 to about 20 mM phosphate. In one embodiment, the equilibration buffer, the load buffer, and the wash buffer comprise about 5 mM of the divalent metal cation, and the elution buffer comprises about 6 mM phosphate. In one embodiment, the load buffer comprises a monovalent cation, such as NaCl or KCl. In some embodiments, the divalent metal cation is either $CaCl_2$ or $MgCl_2$, and in one embodiment, the divalent metal cation is $CaCl_2$. In at least some embodiments, the phosphate is either sodium phosphate or potassium phosphate, and in one embodiment, the phosphate is sodium phosphate.

In some embodiments of the invention, the equilibration buffer, the wash buffer and/or the elution buffer further comprise about 10 mM to about 200 mM HEPES, e.g., about 10 mM HEPES. In at least some other embodiments, the equilibration buffer, the wash buffer and/or the elution buffer have a pH of about 6.1 to about 8.1, e.g., a pH of about 7.2.

In some embodiments of the invention, the acidic protein purified is an immunoglobulin-fusion protein, e.g., receptor fusion protein. In one embodiment of the invention, the receptor fusion protein is ActRIIB-Fc. In another embodiment, the fusion protein is sIL21r-Fc.

In some embodiments of the invention, the hydroxyapatite resin is ceramic hydroxyapatite Type I or Type II. In at least some embodiments, the method further comprises, prior to the step of applying the equilibration buffer, the step of subjecting the protein preparation to a purification method selected from the group consisting of Protein A chromatography, affinity chromatography, hydrophobic interaction chromatography, immobilized metal affinity chromatography, size exclusion chromatography, diafiltration, ultrafiltration, viral removal filtration, ion exchange chromatography, and combinations thereof.

DETAILED DESCRIPTION OF THE INVENTION

Proteins of the Invention

Figure 1:
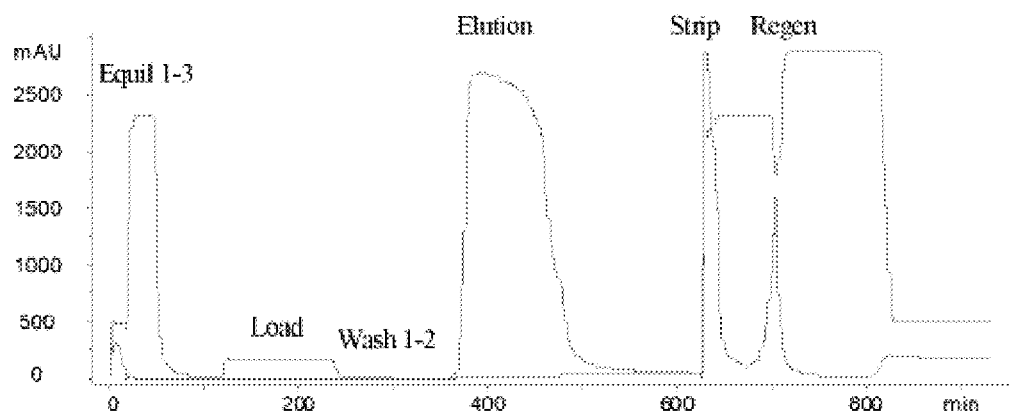
FIG. 1 is a chromatogram from an exemplary $CaCl_2$-charged cHA column run.

Proteins to be purified using the methods of the invention are preferably acidic proteins, e.g., fusion proteins, receptor fusion proteins, immunoglobulin-fusion proteins, soluble receptor fusion proteins, and other polypeptide products.

As used herein, the phrases "polypeptide" or "polypeptide product" are synonymous with the terms "protein" and "protein product," respectively, and, as is generally understood in the art, refer to at least one chain of amino acids linked via sequential peptide bonds. In certain embodiments, a "protein of interest" or a "polypeptide of interest" or the like is a protein encoded by an exogenous nucleic acid molecule that has been transfected or transformed into a host cell, e.g., transiently or stably transfected or transformed into a host cell. In certain embodiments, wherein an exogenous DNA with which the host cell has been transfected or transformed codes for the "protein of interest," the nucleic acid sequence of the exogenous DNA determines the sequence of amino acids. This sequence may be a sequence that occurs in nature, or may alternatively be a sequence engineered by man. In certain embodiments, a "protein of interest" is a protein encoded by a nucleic acid molecule that is endogenous to the host cell or host organism.

In a preferred embodiment of the invention, the protein of interest is an acidic protein. Acidic proteins are proteins that carry a negative charge at a neutral pH and possess an acidic isoelectric point (pI). Commonly, acidic proteins contain higher content of acidic amino acids, such as aspartic and glutamic acid. Because of their negative charge at neutral pH, acidic proteins display distinct binding properties, e.g., distinct properties in chromatographic applications.

In some embodiments of the invention, the protein of interest is a fusion protein. In some embodiments of the invention, the fusion protein is an Ig-fusion protein, such as a receptor fusion protein. In other embodiments, the fusion protein is a soluble fusion protein, e.g., soluble receptor fusion protein.

Fusion proteins, e.g., receptor fusion proteins, can be produced according to methods well known in the art. In one embodiment of the invention, a fusion protein comprises two polypeptide moieties. For example, for a soluble receptor fusion protein, the first moiety comprises a full-length receptor; alternatively, the first moiety comprises less than the full length of the receptor, e.g., an extracellular portion of the receptor. The soluble receptor can also comprise an additional polypeptide (a second moiety), e.g., a GST, Lex-A, MBP polypeptide sequence or an immunoglobulin chain, including, e.g., an Fc fragment, a heavy chain constant region of the various isotypes, including: IgG1, IgG2, IgG3, IgG4, IgM, IgA1, IgA2, IgD, and IgE. In one embodiment of the invention, a soluble receptor fusion protein is an ActRIIB-Fc protein. In another embodiment, the fusion protein is sIL21r-Fc.

In some embodiments, the second moiety of a fusion protein may be an immunoglobulin or a fragment thereof (e.g., an Fc binding fragment thereof). Thus, the terms "immunoglobulin fusion protein," "Ig-fusion protein," "Fc-fusion protein" and the like refer to a protein of interest where the first moiety (i.e., the moiety comprising the polypeptide of interest) is fused to an immunoglobulin or a fragment thereof. Immunoglobulin fusion polypeptides are known in the art and are described in, e.g., U.S. Pat. Nos. 5,516,964; 5,225,538; 5,428,130; 5,514,582; 5,714,147; and 5,455,165.

In some embodiments, the second polypeptide moiety comprises a full-length immunoglobulin polypeptide. Alternatively, the second polypeptide moiety comprises less than the full length of immunoglobulin polypeptide, e.g., a heavy chain, light chain, Fab, $Fab_2$, Fv, or Fc. The second polypeptide moiety can include the heavy chain of an immunoglobulin polypeptide. The second polypeptide moiety can also include the Fc region of an immunoglobulin polypeptide. In some embodiments, the second polypeptide moiety has less effector function than the effector function of an Fc region of a wild-type immunoglobulin heavy chain. Fc effector function includes, for example, Fc receptor binding, complement fixation, and T cell-depleting activity (see, for example, U.S. Pat. No. 6,136,310). Methods for assaying T cell-depleting activity, Fc effector function, and antibody stability are known in the art. In one embodiment, the second polypeptide moiety has low or no affinity for the Fc receptor. In an alternative embodiment, the second polypeptide moiety has low or no affinity for complement protein C1q. The fusion proteins, e.g., soluble receptor fusion proteins, may additionally include a linker sequence joining the soluble receptor or a fragment thereof to the second moiety. For example, the fusion protein can include a peptide linker, e.g., a peptide linker of about 2 to about 20, more preferably about 5 to about 10, amino acids in length.

In another embodiment, the fusion protein may include a heterologous signal sequence at its N-terminus. In certain host cells (e.g., mammalian host cells), expression and/or secretion of the fusion protein, e.g., soluble receptor fusion protein, can be increased through use of a heterologous signal sequence. An example of a signal peptide that can be included in the fusion protein is MKFLVNVALVFMVVYISYIYA (SEQ ID NO:1).

A chimeric or fusion protein of the invention can be produced by standard recombinant DNA techniques. For example, DNA fragments coding for the different polypeptide sequences are ligated together in-frame in accordance with conventional techniques, e.g., by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and reamplified to generate a chimeric gene sequence (see, for example, Ausubel et al. (Eds.) CURRENT PROTOCOLS IN MOLECULAR BIOLOGY, John Wiley & Sons, 1992). Moreover, many expression vectors that encode a fusion moiety (e.g., an Fc region of an immunoglobulin heavy chain) are commercially available.

A protein of interest, e.g., an acidic protein, may be produced by expression in a number of cell lines that may act as suitable host cells. For instance, such cells may be animal cells. The phrase "animal cells" encompasses invertebrate, nonmammalian vertebrate (e.g., avian, reptile and amphibian), and mammalian cells. Nonlimiting examples of invertebrate cells include the following insect cells: *Spodoptera frugiperda* (caterpillar), *Aedes aegypti* (mosquito), *Aedes albopictus* (mosquito), *Drosophila melanogaster* (fruitfly), and *Bombyx mori* (silkworm/silk moth). The polypeptides of interest may be recombinantly produced by operably linking the isolated polynucleotides of interest to suitable control sequences in one or more insect expression vectors, such as baculovirus vectors, and employing an insect cell expression system. Materials and methods for baculovirus/Sf9 expression systems are commercially available in kit form (e.g., the MaxBac® kit, Invitrogen, Carlsbad, Calif.).

In preferred embodiments the host cells are mammalian cells. A number of mammalian cell lines are suitable host cells for recombinant expression of the protein of interest. Mammalian host cell lines include, for example, COS, PER.C6, TM4, VERO076, MDCK, BRL-3A, W138, Hep G2, MMT, MRC 5, FS4, CHO, 293T, A431, 3T3, CV-1, C3H10T1/2, Colo205, 293, HeLa, L cells, BHK, HL-60, FRhL-2, U937, HaK, Jurkat cells, Rat2, BaF3, 32D, FDCP-1, PC12, M1x, murine myelomas (e.g., SP2/0 and NS0) and C2Cl2 cells, as well as transformed primate cell lines, hybridomas, normal diploid cells, and cell strains derived from in vitro culture of primary tissue and primary explants. Numerous cell lines are available from commercial sources, such as the American Type Culture Collection (ATCC). In one embodiment of the invention, the protein of interest is expressed in CHO host cells. Alternatively, it may be possible to recombinantly produce the polypeptides of interest in lower eukaryotes such as yeast or in prokaryotes. Potentially suitable yeast strains include *Saccharomyces cerevisiae, Schizosaccharomyces pombe, Kluyveromyces* strains, and *Candida* strains. Potentially suitable bacterial strains include *Escherichia coli, Bacillus subtilis*, and *Salmonella typhimurium*. If the polypeptides of interest are made in yeast or bacteria, it may be necessary to modify them by, for example, phosphorylation or glycosylation of appropriate sites, in order to obtain functionality. Such covalent attachments may be accomplished using well-known chemical or enzymatic methods.

Expression in bacteria may result in formation of inclusion bodies incorporating the recombinant protein. Thus, refolding of the recombinant protein may be required in order to produce active or more active material. Several methods for obtaining correctly folded heterologous proteins from bacterial inclusion bodies are known in the art. These methods generally involve solubilizing the protein from the inclusion bodies, then denaturing the protein completely using a chaotropic agent. When cysteine residues are present in the primary amino acid sequence of the protein, it is often necessary to accomplish the refolding in an environment that allows correct formation of disulfide bonds (a redox system). General methods of refolding are disclosed in Kohno (1990) *Meth. Enzymol.* 185:187-95. EP 0433225 and U.S. Pat. No. 5,399,677 describe other appropriate methods.

Hydroxyapatite Chromatography Resin

Subsequent to expression of the protein of interest in host cells, the protein of interest, e.g., acidic protein, is purified. The protein of interest may be purified from cell extracts of a host cell line that expresses the protein of interest or conditioned media (harvest media) derived from culturing a recombinant host cell line that expresses the protein of interest. Additionally, the protein of interest may be purified from a number of other sources including, but not limited to, serum of animals, ascites fluid, organ extracts, etc. Common methods of protein purification, such as affinity chromatography, ion exchange chromatography, size exclusion chromatography, and hydrophobic interaction chromatography fail to remove unwanted components from protein preparations, such as high molecular weight aggregates or inactive and/or partially active species. Therefore, the method of the present invention utilizes hydroxyapatite resin for purification of protein of interest, e.g., an acidic protein.

The term "high molecular weight aggregates" or "HMWA" refers to an association of at least two proteins of interest. The association may arise by any method including, but not limited to, covalent, non-covalent, disulfide, or nonreducible crosslinking. "High molecular weight aggregate" may be an association between at least two of the same proteins and/or association between the protein of interest and other proteins found in the cell culture, e.g., host cell proteins.

"Inactive species" and "partially active species" of the protein of interest are proteins that have the same amino acid sequence and molecular weight as the protein of interest, but display no or significantly lower binding capacity, respectively, to target. Significantly lower binding capacity to target, as used herein, refers to at least about 10%, 20% or 30% reduction, preferably at least about 40% reduction, in binding capacity of the partially active protein species as compared to the active protein. "Inactive species" and "partially active species" also refer to proteins that have the same amino acid sequence and molecular weight as the protein of interest, but display no or significantly lower activity, respectively, than the active protein. Significantly lower activity, as used herein, refers to at least about 30% reduction, preferably at least about 40% reduction, in activity of the partially active protein species as compared to the active protein. Percent reduction in binding capacity and/or activity can be measured, for example, by comparing the binding capacity and/or activity of the protein in the peak elution with that of the protein in the strip fraction.

In the method of the present invention, impurities, e.g., high molecular weight aggregates, and inactive and/or partially active species of the protein of interest are successfully separated from the active protein of interest, e.g., an acidic protein, using hydroxyapatite cHA chromatography method.

Various hydroxyapatite chromatographic resins are available commercially, and any available form of the material can be used in the practice of this invention. In one embodiment of the invention, the hydroxyapatite is in a crystalline form. Hydroxyapatites for use in this invention may be those that are agglomerated to form particles and sintered at high temperatures into a stable porous ceramic mass.

However, in a preferred embodiment, the hydroxyapatite is ceramic hydroxyapatite. "Ceramic hydroxyapatite" or "cHA" refers to an insoluble hydroxylated calcium phosphate of the formula $[Ca_{10}(PO_4)_6(OH)_2]$, which has been sintered at high temperatures into a spherical, macroporous ceramic form. The term "cHA" encompasses, but is not limited to, Type I and Type II ceramic hydroxyapatite. Unless specified, "cHA" refers to any particle size including, but not limited to, 20, 40, and 80 μm.

The particle size of the hydroxyapatite may vary widely, but a typical particle size ranges from about 1 μm to about 1,000 μm in diameter, and may be from about 10 μm to about 100 μm. In one embodiment of the invention, the particle size is about 20 μm. In another embodiment of the invention, the particle size is about 40 μm. In yet another embodiment of the invention, the particle size is about 80 μm.

A number of chromatographic supports may be employed in the preparation of cHA columns, the most extensively used are Type I and Type II hydroxyapatite. Type I has a high protein binding capacity and better capacity for acidic proteins. Type II, however, has a lower protein binding capacity, but has better resolution of nucleic acids and certain proteins. The Type II material also has a very low affinity for albumin and is especially suitable for the purification of many species and classes of immunoglobulins. The choice of a particular hydroxyapatite type can be determined by the skilled artisan.

This invention may be used with hydroxyapatite resin that is loose, packed in a column, or in a continuous annual chromatograph. In one embodiment of the invention, ceramic hydroxyapatite resin is packed in a column. The choice of column dimensions can be determined by the skilled artisan. In one embodiment of the invention, a column diameter of at least about 0.5 cm with a bed height of about 20 cm may be used for small scale purification. In an additional embodiment of the invention, a column diameter of from about 35 cm to about 60 cm may be used. In yet another embodiment of the invention, a column diameter of from about 60 cm to about 85 cm may be used. In certain embodiments of the invention, a slurry of ceramic hydroxyapatite resin in about 200 mM $Na_2HPO_4$ solution at pH of about 9.0 may be used to pack the column at a constant flow rate of about 4 cm/min or with gravity.

Hydroxyapatite Chromatography Purification Method

In the method of the present invention, the protein of interest, e.g., an acidic protein, e.g., an acidic immunoglobulin fusion protein, is purified from impurities, such as HMWA, and inactive and/or partially active species, using cHA chromatography in a binding mode.

"Binding mode" refers to a protein preparation separation technique in which at least one protein contained in the preparation binds to a chromatographic resin or support, while at least one contaminant or impurity flows through. Binding mode may be used, for instance, in hydroxyapatite chromatography and ion exchange chromatography.

The present method uses a cHA support charged with a divalent metal solution, e.g., divalent cation solution, at a neutral pH and low ionic strength. For example, divalent cation solutions may be $MgCl_2$ or $CaCl_2$ solutions. A divalent metal cation-charged column is particularly useful for immobilizing acidic proteins of interest because it is able to strengthen the bonding of acidic proteins to cHA due to the formation of additional bridges between protein carboxyls and column phosphate sites. Gorbunoff (1985) *Methods Enzymol.* 182:329-39.

In a preferred embodiment of the invention, the divalent cation solution used to charge the column is a $CaCl_2$ solution. Such $CaCl_2$-charged columns are able to bind the protein of interest, inactive and partially active species, and HMWA. For example, the cHA column may be charged by equilibrating the column with equilibration buffer comprising low ionic strength $CaCl_2$ solution. For example, the $CaCl_2$ solution may be about 1 mM to about 20 mM, preferably about 2 mM to about 10 mM $CaCl_2$. In one embodiment of the invention, the $CaCl_2$ solution is about 5 mM. The equilibration buffer may further comprise about 10 mM to about 200 mM HEPES, preferably up to about 50 mM HEPES, most preferably about 10 mM HEPES. Instead of HEPES, the equilibration buffer may contain any other solvent with buffering capacity. The pH of $CaCl_2$-containing equilibration solution may range from slightly basic to slightly acidic pH. For example, the equilibration buffer pH may range from about 6.1 to about 8.1, preferably the equilibration buffer pH is about 7.2.

Optionally, prior to charging the column with an equilibration buffer comprising the divalent cation solution, e.g., $CaCl_2$ or $MgCl_2$, the column can be equilibrated in two steps by first applying an equilibration solution comprising about 0.1 mM to about 0.5 mM of a phosphate solution and about 0.1 mM to about 2.0 mM of a salt solution in a slightly basic to slightly acidic pH. In one embodiment, about 0.3 M sodium phosphate and about 1.0 M NaCl, at pH of about 6.8 is used. One skilled in the art will understand that the phosphate and salt solutions and the pH used for the first equilibration step would vary depending on the protein of interest. In a second equilibration step, the equilibration buffer may comprise about 10 mM to about 200 mM of buffer, such as up to about 50 mM HEPES, most preferably about 10 mM HEPES, at a slightly basic to slightly acidic pH, such as pH of about 6.1 to about 8.1, preferably about 7.2, or any other solvent with buffering capacity.

In a method of the present invention, after charging the column with a divalent metal cation solution, e.g., a $CaCl_2$ solution, the column may be loaded with the load buffer containing the protein of interest. The load buffer may be any buffer, e.g., a buffer from a previous purification step, such as protein A purification step, spiked with a divalent metal cation. Alternatively, the protein of interest may be buffer exchanged into a load buffer containing a divalent metal cation. Alternatively, the protein of interest can be directly loaded onto the column, without addition of a divalent cation directly to the load buffer. More particularly, the load buffer can comprise a monovalent cation, such as NaCl. Preferably, for purification of sIL21r-Fc, a divalent cation is not added to the load buffer. In another embodiment of the invention, the protein of interest preparation may be spiked or buffer exchanged into a load buffer comprising about 1 mM to about 20 mM of a monovalent or divalent metal cation, such as about 2 mM to about 10 mM $CaCl_2$. In another embodiment of the invention, the protein of interest preparation may be spiked with about 5 mM $CaCl_2$.

Subsequently to loading the column with the load buffer containing the protein of interest, the column is washed with a wash buffer of the same pH and comprising the same divalent metal cation at about the same concentration as the equilibration solution used to charge the column. The wash step is performed in order to remove loosely bound impurities. Thus, the wash buffer may comprise about 1 mM to about 20 mM $CaCl_2$, preferably about 2 mM to about 10 mM $CaCl_2$, most preferably about 5 mM $CaCl_2$. The wash buffer may further comprise about 10 mM to about 200 mM HEPES, preferably up to about 50 mM HEPES, most preferably about 10 mM HEPES. Instead of HEPES, the wash buffer may contain any other solvent with buffering capacity. In one embodiment, the wash buffer is a solution comprising about 5 mM $CaCl_2$, and about 10 mM HEPES, at pH of about 7.2. Subsequently, the column may be washed with another buffer, e.g., about 10 mM to about 200 mM HEPES buffer, preferably up to about 50 mM HEPES, most preferably about 10 mM HEPES buffer, to remove any free $CaCl_2$. pH of the second wash buffer may be about 6.1 to about 8.1, preferably about 7.2. After washing, the protein of interest is eluted with a phosphate-containing elution buffer, e.g., a sodium phosphate-containing buffer or a potassium phosphate-containing buffer. For example, the elution buffer may contain about 2 mM to about 50 mM phosphate buffer. In a preferred embodiment of the invention, the phosphate-containing elution buffer is about 2 mM to about 10 mM sodium phosphate buffer, such as about 6 mM sodium phosphate buffer. The elution buffer may further comprise about 10 to about 200 mM HEPES, preferably up to about 50 mM HEPES, most preferably about 10 mM HEPES. Instead of HEPES, the elution buffer may contain any other solvent with buffering capacity. The pH of the elution buffer may range from slightly basic to slightly acidic pH. For example, the elution buffer pH may range from about 6.1 to about 8.1, preferably the equilibration buffer pH is about 7.2.

After elution of the protein of interest, HMWA, and inactive and/or partially active species are optionally subsequently eluted from the resin.

In addition, the column may optionally be cleaned, i.e., stripped and regenerated, after the elution of the protein of interest. This procedure is typically performed regularly to minimize the building up of the impurities on the surface of the solid phase and/or sterilize the matrix to avoid contamination of the product with microorganisms. The resin is commonly stripped with a sodium phosphate and a salt solution, such as about 0.1 mM to about 0.5 mM sodium phosphate and about 0.1 M to about 2.0 M NaCl solution, such as about 0.3 M sodium phosphate and about 1.0 M NaCl; at a slightly basic to slightly acidic pH, such as pH of about 6.8. The resin is commonly regenerated using a sodium hydroxide and potassium phosphate solution.

Additionally, the resin may be optionally stored between runs in a storage buffer. A storage buffer is commonly a sodium hydroxide buffer, such as about 100 mM sodium hydroxide buffer.

Exemplary components of all buffers are demonstrated in Table 1. Buffer components may be adjusted according to the knowledge of the person of ordinary skill in the art. Not all of the buffers or steps are necessary, but are provided for illustration only. For example, it may not be necessary to have equilibration steps 1 and 2, and it may not be necessary to strip, regenerate, or store the hydroxyapatite resin.

In the method of the present invention, eluted protein of interest, e.g., eluted acidic protein, comprises a reduced level of HMWA and inactive and/or partially active species. In one embodiment, a level of HMWA is reduced by at least 60%, preferably by at least 80%, most preferably by at least 90% (e.g., from about to about 5% to about 15% in the load to less than about 2% in the elution peak). A number of methods can be used to measure the content of HMWA in eluted protein, for example, size exclusion chromatography (SEC-HPLC). A BIACORE (GE-Healthcare, Piscataway, N.J.) assay and binding activity ELISA assays may be used to monitor removal of the inactive and/or partially active species.

Additional Optional Purification Steps

As mentioned above, the cHA-based purification method of the invention can be used in combination with other protein purification techniques. It is desirable for cHA chromatography that the initial load challenges are less or equal than about 40 mg/mL of cHA resin, such as about 20 mg/mL of cHA resin. Therefore, in one embodiment of the invention, one or more steps preceding the hydroxyapatite step may be desirable to reduce the load challenge of the contaminants or impurities. In another embodiment of the invention, one or more purification steps following the hydroxyapatite step may be desirable to remove additional contaminants or impurities.

The cHA purification procedure described may optionally be combined with other purification steps, including but not limited to, Protein A chromatography, affinity chromatography, hydrophobic interaction chromatography, immobilized metal affinity chromatography, size exclusion chromatography, diafiltration, ultrafiltration, viral removal filtration, and/or ion exchange chromatography.

In one embodiment, prior to the cHA purification step, the harvest media for immunoglobulin fusion proteins may be optionally initially purified by a Protein A chromatography step. For example, PROSEP-A (Millipore, U.K.), which consists of Protein A covalently coupled to controlled pore glass, can be usefully employed. Other useful Protein A formulations include Protein A Sepharose FAST FLOW (GE-Healthcare, Piscataway, N.J.), TOYOPEARL 650M Protein A (TosoHaas Co., Philadelphia, Pa.), and MABSELECT columns (GE-Healthcare, Piscataway, N.J.).

As an optional step prior to the cHA purification, ion exchange chromatography may be employed. In this regard various anionic or cationic substituents may be attached to matrices in order to form anionic or cationic supports for chromatography. Anionic exchange substituents include diethylaminoethyl (DEAE), trimethylaminoethyl acrylamide (TMAE), quaternary aminoethyl (QAE) and quaternary amine (Q) groups. Cationic exchange substituents include carboxymethyl (CM), sulfoethyl (SE), sulfopropyl (SP), phosphate (P) and sulfonate (S). Cellulosic ion exchange resins such as DE23, DE32, DE52, CM-23, CM-32 and CM-52 are available from Whatman Ltd. Maidstone, Kent, U.K. Sephadex-based and cross-linked ion exchangers are also known. For example, DEAE-, QAE-, CM-, and SP-Sephadex, and DEAE-, Q-, CM- and S-Sepharose, and Sepharose are all available from Amersham Biosciences, Piscataway, N.J. Further, both DEAE and CM derivitized ethylene glycol-methacrylate copolymer such as TOYOPEARL DEAE-650S or M and TOYOPEARL CM-650S or M are available from Toso Haas Co., Philadelphia, Pa.

In one embodiment of the invention, ion exchange chromatography may be used in binding mode or flow-through mode.

In certain embodiments, the Protein A chromatography step is conducted first, the ion exchange step is conducted second, and the cHA step is conducted third.

Additional Impurities

In addition to HMWA, inactive and/or partially active species removal, cHA chromatography has been shown useful in removing other impurities from protein preparations. Other impurities that may be removed by the cHA chromatography methods of the invention include, but are not limited to, DNA, host cell protein, adventitious viruses, and leached Protein A contaminants from prior purification steps.

In one embodiment of the invention, the method is able to remove leached Protein A from the protein preparation. In certain embodiments of this invention, the amount of leached Protein A present in the final preparation can be reduced significantly, such as from about 28 ppm to about 1 ppm.

In another embodiment of the invention, the method is able to remove host cell protein (HCP) from the protein preparation. In certain embodiments of the invention, the amount of HCP in the final preparation can be reduced from about 7500 ppm to about 750 ppm. HCP and Protein A ELISA assays may be used to monitor the removal of HCP and leached Protein A.

EXAMPLE

The Example which follows is set forth to aid in the understanding of the invention but is not intended to, and should not be construed to, limit the scope of the invention in any way. The Example does not include detailed descriptions of conventional methods, e.g., cloning, transfection, basic aspects of methods for overexpressing proteins in cell lines, and methods for conducting any additional preliminary purification steps (such as Protein A chromatography). Such methods are well known to those of ordinary skill in the art.

Example 1

An acidic immunoglobulin fusion protein, ActRIIB-Fc, was expressed in CHO cells and purified from the harvest media by rProtein A chromatography (GE-Healthcare, Piscataway, N.J.). The protein elution from rProtein A chromatography, which contained ActRIIB-Fc protein, also contained a significant level of inactive and partially active species and HMWA (see "Load" row in Table 2). In order to remove inactive and partially active ActRIIB-Fc species and HMWA, the elution from the Protein A column was subjected to cHA chromatography.

The cHA column (BioRad Laboratories, Hercules, Calif.) was first equilibrated with Equilibration Buffer 1, containing 0.3 M sodium phosphate, 1.0 M NaCl, pH 6.8, followed by Equilibration Buffer 2, containing 10 mM HEPES, pH 7.2 (Table 1). Equilibration Buffer 1 is a buffer with high concentration of phosphate and the Equilibration Buffer 2 is used to wash out the phosphate. The column was subsequently equilibrated with calcium chloride solution at neutral pH and low ionic strength (Equilibration Buffer 3, containing 5 mM $CaCl_2$ and 10 mM HEPES, pH 7.2) to prepare the column for loading. The rProtein A eluate pool was adjusted to contain 5 mM calcium chloride (Load) and loaded onto the cHA column. Under the loading buffer condition, both the product, product-related impurities (inactive and partially active species and HMWA), and the process-derived impurities (leached protein A, host cell proteins and DNA) were bound to the cHA resin. The column was then washed with a calcium chloride buffer (Wash 1), followed by a second wash buffer (Wash 2) to remove the calcium chloride, and the active product, i.e., active ActRIIB-Fc, was selectively eluted using 6 mM sodium phosphate and 10 mM HEPES buffer at neutral pH of 7.2 (Elution). The product-related impurities, including the inactive and partially active species and HMWA species, were subsequently stripped off the resin using a higher concentration of phosphate buffer. Lastly, the resin was regenerated using a sodium hydroxide and potassium phosphate solution.

TABLE 1

List of Buffers for the cHA Step

| Buffer | Composition |
|---|---|
| Equilibration Buffer 1 | 0.3 M Sodium Phosphate, 1.0 M NaCl, pH 6.8 |
| Equilibration Buffer 2 | 10 mM HEPES, pH 7.2 |
| Equilibration Buffer 3 | 5 mM $CaCl_2$, 10 mM HEPES, pH 7.2 |
| Load | Buffer comprising protein of interest, 5 mM $CaCl_2$ |
| Wash 1 | 5 mM $CaCl_2$, 10 mM HEPES, pH 7.2 |
| Wash 2 | 10 mM HEPES, pH 7.2 |
| Elution | 6 mM Sodium Phosphate, 10 mM HEPES, pH 7.2 |
| Strip | 0.3 M Sodium Phosphate, 1.0 M NaCl, pH 6.8 |
| Regeneration | 0.5 M Potassium Phosphate, 1.0 M NaOH |
| Storage | 100 mM NaOH |

FIG. 1 shows a chromatogram from the cHA column run. The majority of the product of interest is eluted in the elution fraction while the strip fraction contains both the inactive and partially active species (monomer), and the HMWA.

Results of impurity clearance by the cHA chromatographic step under the defined operating conditions are listed in Table 2. BIACORE assay (GE-Healthcare, Piscataway, N.J.) was used to monitor the removal of inactive and partially active species, SEC-HPLC (Waters Corporation, Milford, Mass.) was used to measure the HMWA content, and host cell protein (HCP) and protein A ELISA assays were used to monitor the removal of HCP and leached Protein A. The monomer in the load and strip fraction was isolated from the HMWA and then tested by BIACORE assay for binding activity. As shown in Table 2, the product of interest in the elution fraction has a much higher binding activity than the inactive and partially active species present in the strip pool. The cHA step was run in pilot and clinical manufacturing scale. Data generated from the large scale cHA column runs were shown in Table 3.

TABLE 2

Results of Impurity Clearance from a CaCl₂ Charged cHA Column Run

| | Binding Activity by BIACORE ™ (RU) | Relative Activity (%) | HCP (ppm) | Leached protein A (ppm) | % HMWA |
|---|---|---|---|---|---|
| Load | Not tested (NT) | NA | 7500 | 28 | 5 |
| Peak pool | 62 | 100 | 748 | 1.2 | 0.24 |
| Strip pool | 36 | 58 | NT | NT | 14.5 |

TABLE 3

Results of impurity clearance from a CaCl2 charged cHA column in larger scale operation

| Samples | Rmax (RU) | Relative Activity (%) | HCP (ppm) | Leached protein A (ppm) | % HMWA |
|---|---|---|---|---|---|
| Batch 1-load | 61 | 94 | 4867 | 12 | 4.9 |
| Batch 1-Peak | 65 | 100 | 1044 | 0.6 | 0.3 |
| Batch 1-Strip | 55 | 85 | NT | NT | NT |
| Batch 2-load | 62 | 94 | 5840 | 5 | 3.9 |
| Batch 2-Peak | 66 | 100 | 1015 | 0.7 | 0.8 |
| Batch 2-Strip | 56 | 85 | NT | NT | NT |
| Batch 3-load | 60 | 94 | 2006 | 14 | 3.9 |
| Batch 3-Peak | 64 | 100 | 273 | 2 | 0.4 |
| Batch 3-Strip | 50 | 78 | 4071 | 36 | NT |
| Batch 4-Load | 60 | 92 | 2969 | 16 | 4.1 |
| Batch 4-Peak | 65 | 100 | 289 | 3 | 0.4 |
| Batch 4-Strip | 48 | 74 | 4239 | 38 | NT |

Example 2 cHA chromatography was found to be superior for HMWA removal during purification of another acidic Ig fusion protein comprising IL21 fused to the Fc domain of Ig (sIL21r-Fc). See Ettinger et al., Ann Rheum Dis 2008; 67 (Suppl III):iii83-iii86 (for a description of the sIL21r-Fc fusion protein). One goal for this process step was to remove HMWA in order to improve the subsequent chromatographic step's capacity for HMWA and HCP. The column was equilibrated with a calcium chloride solution at neutral pH and low ionic strength. The rProtein A eluate pool was not spiked with calcium chloride for this process due to observed product instability upon exposure to calcium chloride, but rather, the rProtein A eluate pool was loaded directly onto the cHA column at 20-30 g/L resin load challenge. Under these buffer conditions, the product was bound to the cHA resin, with some species of HMWA flowing through the column. The column was then washed with a neutral pH and low ionic strength buffer and the active product was selectively eluted using a 10-17 mM phosphate buffer at neutral pH. Additional species of HMWA were subsequently stripped off the resin using a higher concentration of phosphate buffer. Lastly, the resin was regenerated using a sodium hydroxide and potassium phosphate solution.

TABLE 3

Figure 2:
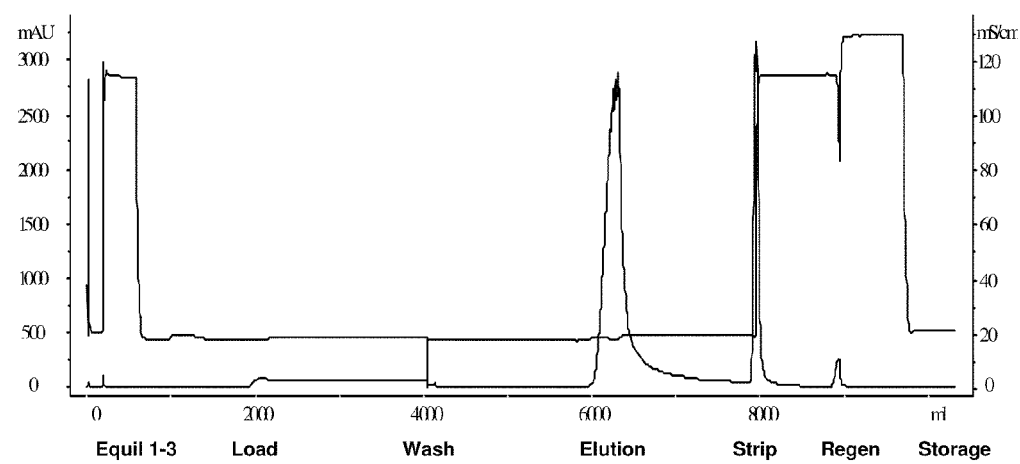
FIG. 2 is a cHA chromatogram for purification of an acidic Ig fusion protein (sIL21rFc).

List of Buffers for the cHA Step of purification of sIL21r-Fc (FIG. 2)

| Buffer | Composition |
|---|---|
| Equilibration 1 | 1M Potassium Phosphate, pH 7.2 |
| Equilibration 2 | 50 mM HEPES, 200 mM NaCl, pH 7 |
| Equilibration 3 | 2-10 mM CaCl2, 50 mM HEPES, 200 mM NaCl, pH 7 |
| Load | Protein A peak pool |
| Wash 1 | 50 mM HEPES, 200 mM NaCl, pH 7 |
| Elution | 10-17 mM Sodium Phosphate, 50 mM HEPES, 200 mM NaCl, pH 7 |
| Strip | 1M Potassium Phosphate, pH 7.2 |
| Regeneration | 0.5 M Potassium Phosphate, 1.0 M NaOH, |
| Storage | 100 mM NaOH |

The following table (4) provides results for the purification of sIL21r-Fc purification, illustrated in FIG. 2.

TABLE 4

Results of impurities clearance from the sIL21r-Fc cHA experiments

| | HCP (ppm) | Leached protein A (ppm) | % HMW1 | % HMW2 |
|---|---|---|---|---|
| Load | 90,000 | 3 | 3 | 13-15 |
| Load Eluate | NT | NT | 40-50 | 50-60 |
| Peak | 12,000-17,000 | 0.7-1.1 | 0.6-0.7 | 4-5 |
| Strip | NT | NT | 6-7 | 30-40 |

What is claimed is:

1. A method of purifying at least one acidic protein of interest from a protein preparation containing impurities, comprising:
   (a) applying an equilibration buffer comprising $CaCl_2$ to hydroxyapatite resin;
   (b) contacting the hydroxyapatite resin with the protein preparation in a load buffer;
   (c) washing the hydroxyapatite resin with a wash buffer comprising $CaCl_2$; and
   (d) eluting at least one acidic protein from the hydroxyapatite resin with an elution buffer comprising about 2 to about 50 mM phosphate.

2. The method of claim 1, wherein the equilibration buffer comprises from about 1 to about 20 mM $CaCl_2$, the load buffer comprises about 1 to about 20 mM $CaCl_2$, and the wash buffer comprises about 1 to about 20 mM $CaCl_2$.

3. The method of claim 2, wherein the equilibration buffer, the load buffer, and the wash buffer comprise about 5 mM $CaCl_2$, and the elution buffer comprises about 6 mM phosphate.

4. The method of claim 1, wherein the impurities are inactive or partially active species of the at least one acidic protein.

5. The method of claim 1, wherein the impurities are high molecular weight aggregates.

6. The method of claim 5, wherein the method results in at least about 60% reduction in high molecular weight aggregates.

7. The method of claim 6, wherein the method results in at least about 90% reduction in high molecular weight aggregates.

8. The method of claim 1, wherein the hydroxyapatite resin is ceramic hydroxyapatite Type I or Type II.

9. The method of claim 1, wherein the phosphate is sodium phosphate or potassium phosphate.

10. The method of claim 9, wherein the phosphate is sodium phosphate.

11. The method of claim 1, wherein at least one of the equilibration buffer, the wash buffer, or the elution buffer further comprise about 10 mM to about 200 mM HEPES.

12. The method of claim 11, wherein at least one of the equilibration buffer, the wash buffer, or the elution buffer further comprise about 10 mM HEPES.

13. The method of claim 1, wherein at least one of the equilibration buffer, the wash buffer, or the elution buffer have a pH of about 6.1 to about 8.1.

14. The method of claim 13, wherein at least one of the equilibration buffer, the wash buffer, or the elution buffer have a pH of about 7.2.

15. The method of claim 1, wherein the acidic protein is an immunoglobulin fusion protein.

16. The method of claim 15, wherein the immunoglobulin fusion protein is a receptor fusion protein.

17. The method of claim 16, wherein the receptor fusion protein is ActRIIB-Fc.

18. The method of claim 15, wherein the fusion protein is sIL21r-Fc.

19. The method of claim 18, wherein the load buffer comprises a monovalent cation.

20. The method of claim 19, wherein the monovalent cation is NaCl.

21. The method of claim 1, wherein the impurities are protein A or host cell proteins.

22. The method of claim 1, wherein the method further comprises, prior to the step of applying the equilibration buffer, the step of subjecting the protein preparation to a purification method selected from the group consisting of Protein A chromatography, affinity chromatography, hydrophobic interaction chromatography, immobilized metal affinity chromatography, size exclusion chromatography, diafiltration, ultrafiltration, viral removal filtration, ion exchange chromatography, and combinations thereof.

23. A method of purifying at least one acidic protein of interest from a protein preparation containing inactive or partially active species of the at least one acidic protein, comprising:
   (a) applying an equilibration buffer comprising $CaCl_2$ to hydroxyapatite resin;
   (b) contacting the hydroxyapatite resin with the protein preparation;
   (c) washing the hydroxyapatite resin with a wash buffer comprising $CaCl_2$; and
   (d) eluting the at least one acidic protein of interest separately from the inactive or partially active species.

* * * * *